United States Patent [19]

Heiliger et al.

[11] Patent Number: 5,380,924
[45] Date of Patent: Jan. 10, 1995

[54] POLYMERIZABLE EMULSIFIERS AND REACTIVE GROUPS AND POLYMERS OF EMULSIFIERS AND OTHER MONOMERS

[75] Inventors: Ludger Heiliger, Leverkusen; Adolf Schmidt, Cologne; Joachim Probst, Leverkusen, all of Germany

[73] Assignee: Bayer Aktiengesellschaft, Leverkusen, Germany

[21] Appl. No.: 3,641

[22] Filed: Jan. 13, 1993

[30] Foreign Application Priority Data

Jan. 25, 1992 [DE] Germany .................. 4202050

[51] Int. Cl.⁶ .......................... C07C 275/16
[52] U.S. Cl. .................. 562/439; 554/106; 560/33; 562/44; 562/47
[58] Field of Search .............. 562/439, 44, 47; 554/106; 560/33

[56] References Cited

U.S. PATENT DOCUMENTS

| | | | |
|---|---|---|---|
| 4,070,388 | 1/1978 | Jones | 554/106 |
| 4,404,109 | 9/1983 | Tellier et al. | 554/106 |
| 4,429,096 | 1/1984 | Schaefer | 526/287 |
| 4,511,730 | 4/1985 | Fields | 560/33 |
| 4,604,439 | 8/1986 | Colvin et al. | 526/2881 |
| 4,714,772 | 12/1987 | Colvin et al. | 558/240 |
| 4,962,154 | 10/1990 | Pollock | 525/54.1 |
| 4,980,497 | 12/1990 | Sasagawa et al. | 560/33 |
| 5,191,083 | 3/1993 | Colvin et al. | 546/222 |
| 5,237,090 | 8/1993 | Swarup et al. | 560/32 |

FOREIGN PATENT DOCUMENTS 0351534  1/1990  European Pat. Off. ............ 560/33
2075970 11/1981  United Kingdom .

OTHER PUBLICATIONS

Upson, J. Poly. Sci. 72:45–54 (1985).
DeWinter et al, Makromol. Chem. 5:593–596 (1984).
C. Pichot, Makromol. Chem. 35/36:327–347 (1990).

*Primary Examiner*—José G. Dees
*Assistant Examiner*—Barbara S. Frazier
*Attorney, Agent, or Firm*—Connolly & Hutz

[57] ABSTRACT

New compounds corresponding to formula (I)

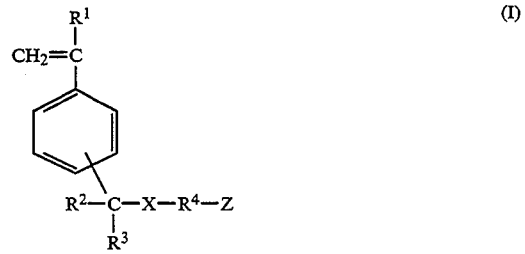

and their use as emulsifiers for aqueous emulsions and, in the case of carboxylic acid derivatives, also as reactive groups for linking to biologically active substrates. New polymers synthesized from the emulsifiers and other monomers are also claimed.

10 Claims, No Drawings

POLYMERIZABLE EMULSIFIERS AND REACTIVE GROUPS AND POLYMERS OF EMULSIFIERS AND OTHER MONOMERS

This invention relates to polymerizable sulfonic and carboxylic acid derivatives, to processes for their production and to their use as emulsifiers for aqueous emulsions and, in the case of carboxylic acid derivatives, also as reactive groups for linkage to biologically active substances, such as proteins and nucleic acids. The invention also relates to polymers synthesized from the emulsifiers and other monomers.

Polymerizable hydrophilic monomers and polymerizable surface-active monomers are known (D. A. Upson, J. Polym. Sci., Polymer. Symp. 72 45 (1985)). However, they are subject to limitations which severely restrict their usefulness. Hydrophilic, i.e. water-soluble, monomers and hitherto known polymerizable emulsifiers, which in their polymerizable part consist either of polar (meth)acrylic groups or of olefinic double bonds plus one other ionic group responsible for the emulsifying property, have the undesirable property of entering into polymerization in the aqueous phase as a secondary reaction instead of undergoing the desired polymerization into the latex phase (C. Pichot, Makromol. Chem., Macromol. Symp. 35/36, 327 (1990)). This is ecologically and economically unacceptable because polymeric contamination of the aqueous serum can lead to disposal problems, in addition to which this component present in the serum is basically a reactant that is inaccessible or only partly accessible to the actual reaction (i.e. synthesis of a latex).

Accordingly, hitherto known emulsifiers also cannot be used for linkage reactions to biologically active substances, instead additional copolymerizable reactive groups have to be added to the polymerization mixture (U.S. Pat. No. 4,962,154) or introduced in a following step. This requires additional effort at the synthesis stage, particularly in regard to the accessibility of the reactive group to the linkage reaction with the biologically active substance in aqueous phase which can only take place at the polymer surface.

It is known that the polymerizability of unactivated apolar olefinic double bonds is very limited on account of the hydrogen atoms present in the allyl position which have a tendency towards transfer reactions. In extreme cases, the effect of this is that only one emulsifier molecule is incorporated per polymer chain (W. de Winter, A. Marien, Makrom. Chem. Rapid. Commun. 5, 593, (1984)). Accordingly, the molecular weights of the polymers in the latex phase are basically limited to low values and/or part of the emulsifier is not covalently bonded to the latex, but instead is merely physically adsorbed. Accordingly, it is present in the aqueous serum in accordance with the distribution equilibrium.

By contrast, compounds according to the present invention have apolar (alpha-methyl-) styrene-functional polymerizable groups which are excellently copolymerizable with the usual latex monomers, such as for example (alpha-methyl-) styrenes and (meth)acrylates. The compounds according to the invention have no tendency to polymerize in the aqueous serum phase. Accordingly, the aqueous phase is almost completely free from residues of emulsifier which is an ecological advantage. In addition, the chemical linkage of these emulsifiers increases the electrolyte and shear stability of the latices and makes them re-emulsifiable in a completely reversable manner.

In addition, compounds according to the invention which contain a carboxylic acid group can be chemically linked to biologically active substances, such as proteins or aminofunctionalized nucleic acids, in aqueous phase, for example by known N-hydroxysuccinimide activation. This provides for improved coupling of these biologically active substances to latices or, generally, to synthetic polymers which are produced using compounds according to the invention. No additional reactive monomers are required because compounds according to the invention are accessible to the coupling reaction by virtue of their surface-active properties. Accordingly, the biologically active substances can be marked with polymers which can be used for their immobilization and/or for detection reactions.

The compounds according to the invention correspond to general formula (I)

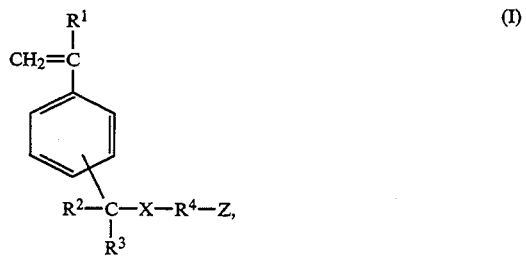

in which

X is NH—CO—Y or Y,

Y is NH, oxygen or sulfur,

Z is COOM or SO$_3$M,

M is hydrogen, sodium, ammonium or potassium,

R$^1$, R$^2$ and R$^3$ independently of one another represent hydrogen or methyl and R$^4$, is C$_{1-12}$ alkylene, C$_{3-12}$ cycloalkylene, phenylene or naphthylene.

Preferred compounds of formula (I) are those in which

X is NH—CO—NH or NH—CO—O; R$^1$, R$^2$ and R$^3$ are methyl and R$^4$ is

C$_{2-11}$ alkylene, more particularly C$_5$H$_{10}$ or C$_{10}$H$_{20}$, or phenylene and the group

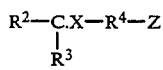

is in the meta position .

Particularly preferred compounds of formula ( I ) are those in which Z stands for COOM and M stands for sodium, potassium or ammonium.

The following compounds are mentioned in particular:

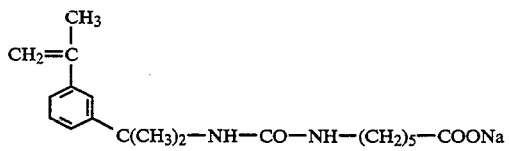

-continued

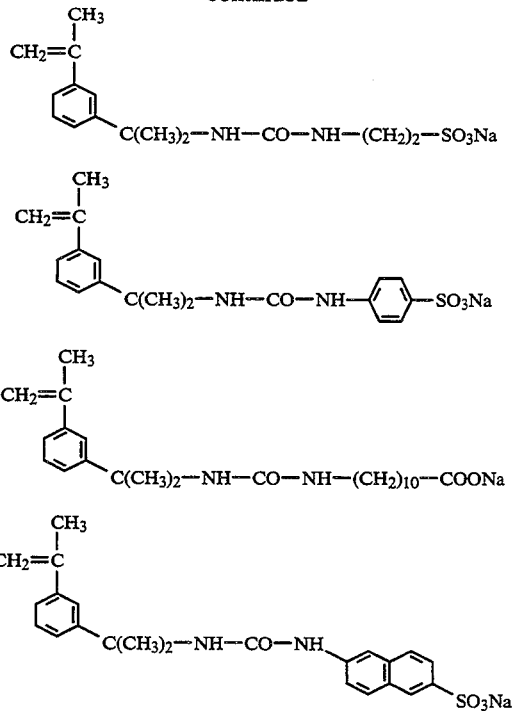

The present invention also relates to a process for the production of compounds according to the invention, characterized in that styrene derivatives corresponding to formula (II)

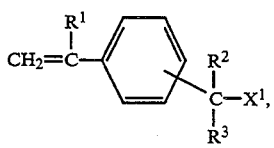

(II)

in which
X$^1$ is NCO or chlorine and
R$^1$, R$^2$ and R$^3$ independently of one another represent hydrogen or methyl,
are reacted with aminosulfonic or aminocarboxylic acids or hydroxysulfonic or hydroxycarboxylic acids corresponding to formula (III)

$$X^2—R^4—Z \quad (III)$$

in which
X$^2$ is OH or NH$_2$,
R$^4$ is C$_{1-12}$ alkylene, C$_{3-12}$ cycloalkylene, phenylene or naphthylene and
Z represents SO$_3$M or COOM and
M is hydrogen, sodium, potassium or ammonium.

The experimental conditions under which compounds according to the invention are prepared correspond to those of additions to isocyanates, ether-forming reactions and alkylations of amines which are all known. For example, the isocyanate is reacted with the amine or alcohol to be reacted in an inert organic solvent, for example from the group consisting of ketones, sulfoxides, amides, ethers or haloalkanes, at temperatures of 20° to 200° C.

Where acids containing amino groups are used, the amino group must be converted into its free form with an equivalent of an auxiliary base, such as sodium hydroxide for example, before the esterification. It can also be of advantage to carry out the esterification in a two-phase reaction (water/methylene chloride) and to add a phase transfer catalyst, such as benzyl trimethyl ammonium hydroxide for example.

The compounds according to the invention may generally be obtained in pure form by evaporation of the solvent or may even be directly used in aqueous solution for emulsification.

The present invention also relates to the use of compounds of general formula (I) according to the invention as emulsifiers for aqueous polymerization. Compounds of formula (I) according to the invention, in which Z represents COOM, may also be used as reactive groups for linking biologically active substrates to synthetic polymers or latices thereof.

The biologically active substrates may be linked to the polymers containing the reactive group by activation of the carboxylic acid group with N-hydroxysuccinimide/dicyclohexyl carbodiimide. The polymer with the ester thus activated may be linked to biologically active substrates, for example through the primary amino groups of many biologically active substances, with elimination of N-hydroxysuccinimide succinimide and formation of an amide bond. Poly(meth)acrylates, polyacrylonitrile, polyacrylamide, polyamide or polystyrene and derivatives thereof or latices thereof are mentioned as examples of synthetic polymers. If the polymer contains one or more fluorophores for example, the biologically active molecule can be detected by fluorescence spectroscopy. This detection is important for diagnostic applications in the medical field.

Compounds of general formula (I) according to the invention can be used for the production of completely redispersible latices, i.e. the latices can be precipitated in a completely reversible manner by pH reduction or by increasing ionic strength and can be re-emulsified by an increase in pH or by dilution without any change in the physical properties of the latices. By virtue of their improved stability to shear forces, electrolytes and temperature influences (thawing and freezing), emulsions such as these may be used as waterborne lacquers (building protection, industrial painting), leather finishes and paper coating compositions. Latices having a solids content of substantially 100% can be produced with compounds according to the invention.

Accordingly, compounds according to the invention are suitable for the production of polymers from industrially important monomers, such as for example styrene, acrylonitrile, (meth)acrylates, (meth)acrylamides, butadiene, vinyl chloride and vinyl acetate and mixtures thereof. Polymers of the compounds of formula (I) according to the invention and other monomers as co-monomers (cf. for example the monomers mentioned above and in the following) are also the subject of the present invention.

Examples of fluorescent comonomers are (meth)acrylates and/or (meth)acrylamides which, through ester or amide bonding, contain coumarins corresponding to formula (IV)

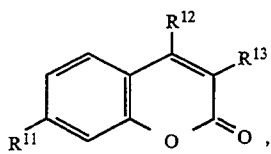 (IV)

in which
R¹¹ represents O alkyl, N(alkyl)₂, NH alkyl, NH—SO₂ alkyl, O trimethyl silyl or NH—SO₂ aryl,
R¹² is hydrogen, cyano, chlorine, hydroxy, alkyl or aryl and
R¹³ is phenyl or hetaryl.

Alkyl is preferably $C_{1-6}$ alkyl, aryl is preferably phenyl, alkylene is preferably $C_{1-6}$ alkylene and hetaryl is preferably (benz)thiazolyl,

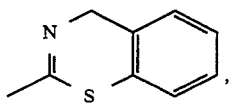

in addition to which
R¹¹ may represent

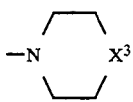

where
X³ is oxygen, N—$C_{1-4}$ alkyl or $(CH_2)_n$ with n=0 or 1.

Other suitable comonomers are (meth)acrylates and/or (meth)acrylamides which also contain coumarins corresponding to formula (V)

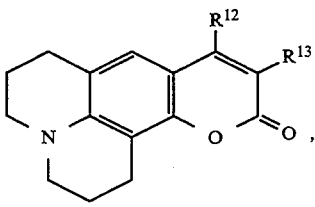 (V)

in which
R¹² and R¹³ have the meanings defined for formula (IV), through ester or amide bonding.

The coumarins corresponding to formulae (IV) and (V) preferably contain a functional group at one of the substituents R¹¹, R¹² and R¹³ for linking the dye to the (meth)acrylic acid or to reactive derivatives thereof or to the polymer obtainable therefrom. NH₂ or OH groups are particularly suitable for this purpose.

Other suitable comonomers are (meth)acrylates and/or (meth)acrylamides containing carbostyrils corresponding to formula (VI)

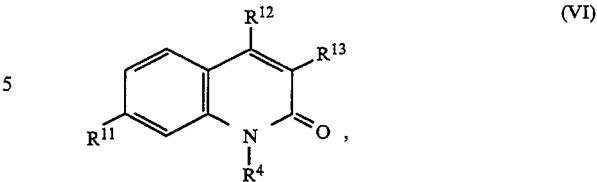 (VI)

in which
R¹¹, R¹² and R¹³ have the meanings defined for the coumarins (see formulae (IV) and (V)) and
R¹⁴ is alkyl, preferably $C_{1-6}$ alkyl.

In this case, too, one of the substituents preferably contains a functional group for linkage to the (meth)acrylic acid or to reactive derivatives thereof or to the polymer obtainable therefrom.

Other suitable comonomers are (meth)acrylates and/or (meth)acrylamides which, through ester or amide bonding, contain pyrazolines corresponding to formula (VII)

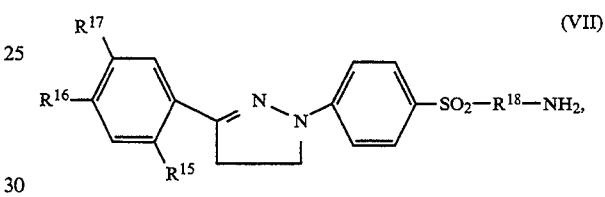 (VII)

in which
R¹⁵ is hydrogen or methyl,
R¹⁶ and R¹⁷ independently of one another represent hydrogen or chlorine and
R¹⁸ represents alkylene,

or alkylene-O-alkylene
where alkyl and alkylene are preferably $C_{1-6}$ alkyl or $C_{1-6}$ alkylene.

Also suitable are naphthalimides corresponding to formula (VIII)

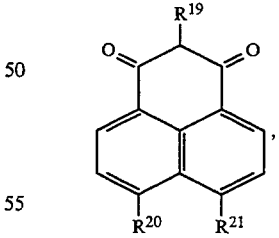 (VIII)

in which
R¹⁹ is alkyl and
R²⁰ and R²¹ independently of one another represent hydrogen, O alkyl or N(alkyl)₂ where alkyl is preferably $C_{1-6}$ alkyl,
one of the substituents R¹⁹, R²⁰ or R²¹ bearing an NH₂ group for linkage to the (meth)acrylic acid or to reactive derivatives thereof or to the polymer obtainable therefrom.

Also suitable are pyrenes corresponding to formula (IX)

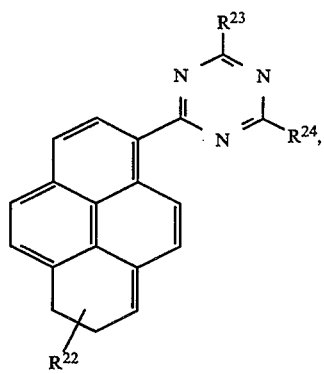

in which

R²² is hydrogen or SO₃H and

R²³ and R²⁴ independently of one another represent O alkyl or N(alkyl)₂ where alkyl is preferably $C_{1-6}$ alkyl, one of the substituents R²³ or R²⁴ bearing an NH₂ group for linkage to the (meth)acrylic acid or to reactive derivatives thereof or to the polymer obtainable therefrom.

Other suitable comonomers are fluoresceins corresponding to formula (X)

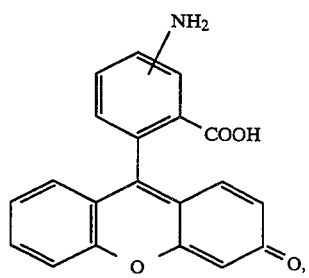

(X)

and rhodanines corresponding to formula (XI)

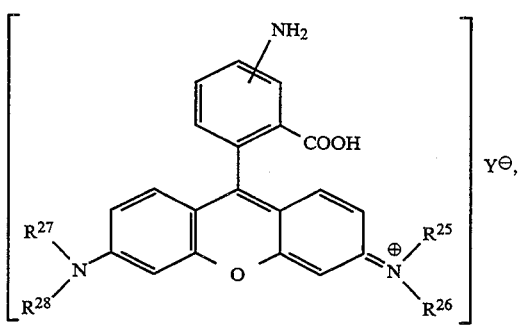

(XI)

in which

Y⊖ is a colorless anion, for example Cl⊖, Br⊖, I⊖, HSO₄⊖,

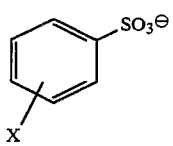

X = Cl, Br, I, CH₃ and

R²⁵ to R²⁸ independently of one another represent alkyl or

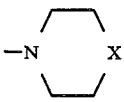

where alkyl is preferably $C_{1-6}$ alkyl and X is oxygen, N—$C_{1-4}$ alkyl or $(CH_2)_n$ with n=0 or 1.

⊕ NR²⁵R²⁶ and/or NR²⁷R²⁸ together with the aromatic ring to which they are attached may also form a polycyclic system, for example a system corresponding to formula (XII) or (XIII)

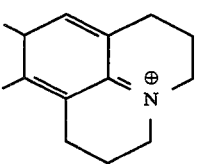

(XII)

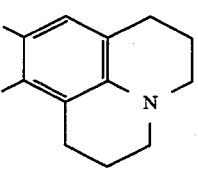

(XIII)

These and other suitable dyes are known (see, for example, "The Chemistry of Synthetic Dyes", Vol. V, Academic Press (1971) and "Fluorescent Whitening Agents", G. Thieme Verlag Stuttgart (1975)).

The compounds mentioned in this connection contain a functional groups at one of the constituents for linkage to the (meth)acrylic acid or to reactive derivatives thereof or to the polymer obtainable therefrom. NH₂ or OH groups are particularly suitable for this purpose.

The percentage content of polymerizable emulsifiers corresponding to formula (I) in the polymers mentioned above is generally from 0.1 to 50% by weight, preferably from 1 to 25% by weight and, more preferably, from 2.5 to 10% by weight.

The polymers may be linear, branched or crosslinked and may be produced by radical polymerization.

Uncrosslinked polymers have average molecular weights (e,ovs/M/ $_w$) in the range from 1,000 to 10,000,000 and preferably in the range from 5,000 to 2,000,000.

The polymers may be produced in organic solvents such as, for example, aromatic hydrocarbons, dimethyl sulfoxide, dimethyl formamide, esters or ketones and may then be dissolved in and allowed to recrystallize from water or may even be directly prepared as a latex in water.

The invention is illustrated by the following Examples.

A) Synthesis of emulsifiers from:

EXAMPLES 1–4

1: TMI + H₂N—(CH₂)₅—COONa
 (TMI = m-isopropenyl-alpha, alpha-dimethylbenzyl isocyanate)

2: TMI + H₂N—(CH₂)₁₀—COONa

3: TMI + H₂N—C₂H₄—SO₃Na

4: TMI + H₂N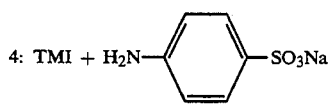SO₃Na 100 ml acetone were added under nitrogen to a solution of 0.1 mol of the above aminocarboxylic or sulfonic acids and 0.1 mol sodium hydroxide in 100 ml deionized water, followed by stirring for 5 minutes. 0.1Mol m-isopropenyl-alpha, alpha-dimethyl benzyl isocyanate dissolved in 50 ml acetone is then added dropwise and, after stirring for 1 hour, the acetone is distilled off.

For IR and NMR spectroscopy, parts of the solution are concentrated by evaporation to dryness. In these residues, the isocyanate band in the IR spectrum at 2,200 cm$^{-1}$ is replaced by a urea band at 1,680 cm$^{-1}$. In the $^1$H-NMR spectrum, the characteristic urea proton resonances are at 6.3 and 6.7 mm.

B) Latex polymerizations

EXAMPLES 5-12

8.94 g of a 1% by weight aqueous sodium carbonate solution and 22.8 g or 34.2 g of a 10% aqueous emulsifier solution of Examples 1 to 4 are added with stirring to 187.34 or 117.08 ml deionized water. 57 g styrene and 11.4 g of a 1% by weight aqueous potassium persulfate solution are then added and, after heating to 70° C., the mixture is polymerized for 19 h. After cooling, the crude latex is filtered through a 100 μ mesh polyamide net and the filtrate is examined for solids content and average particle diameter (Table 1).

The latices of Examples 5 to 12 have a solids content of virtually 100% of the theoretical.

TABLE 1

| Latices of styrene and emulsifiers of Examples 1 to 4 | | | |
|---|---|---|---|
| Latex Example | Emulsifier of Example | Emulsifier content (g solids) | Average particle size in nm (photometry at 700 nm) |
| 5 | 1 | 2.28 | 125 |
| 6 | 1 | 3.42 | 105 |
| 7 | 2 | 2.28 | 144 |
| 8 | 2 | 3.42 | 130 |
| 9 | 3 | 2.28 | 194 |
| 10 | 3 | 3.42 | 207 |
| 11 | 4 | 2.28 | 59 |
| 12 | 4 | 3.42 | 55 |

Redispersion tests:

Quantities of 10 ml of the latices of Examples 5 to 12 are dried in a high vacuum at room temperature and redispersed by addition of 10 ml water. The redispersed latices show no signs of coagulation and have the same average particle size diameters as the respective starting latices.

Serum tests:

The serum investigated by ultracentrifugation did not contain any soluble components and, after concentration by evaporation in a high vacuum, did not show any traces of organic compounds ($^1$H-NMR, thin-layer chromatography)

c) Compounds of formula (I) with z =COOM as reactive group

EXAMPLE 13

Preparation of marking reagent containing emulsifier 1 as linking group for biologically active molecules 1 g of a dye corresponding to the formula

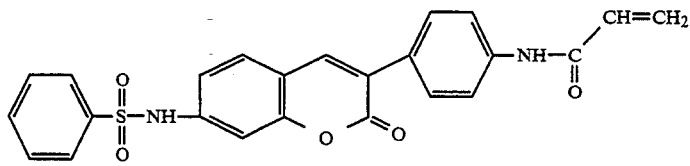

200 mg of the emulsifier of Example 1, 2.8 g sodium p-styryl sulfonate (Na—PSS) and 12 mg azo-isobutyrodinitrile (AIBN) are introduced into 25 ml dimethyl sulfoxide, the reactor is evacuated and purged with nitrogen. This operation is repeated 3 times, after which the solution is heated to 65° C. and reacted for 15 h. After cooling, 150 mg bis-(N-succinimidyl)-carbonate are added to the solution which is then stirred for 6 h at room temperature. The reaction solution is added dropwise to 200 ml methanol and the precipitate formed is filtered off and dried. The crude polymer is subjected to ultrafiltration (cutoff 10,000 dalton). Yield 80%.

EXAMPLE 14

Use of the marking reagent of Example 13 in immunological test systems 10 mg of the polymer of Example 13 are dissolved in 10 ml carbonate/bicarbonate buffer pH 9.0/0.5 molar. 5 mg phosphordiesterase (PDE; from rattlesnake poison (Sigma) in 5 ml carbonate buffer pH 9.0 (0.5M) are then added and, after stirring at room temperature for 4 h, the mixture is placed in a refrigerator and left to react overnight. The crude solution is then adjusted to pH 11 with 1N NaOH and chromatographed (Seplacryl S-500, a product of Pharmacia, in carbonate buffer 0.02M, pH 11, Φ of the column 16 mm, height 100 cm).

After 500 ml of the carbonate buffer have passed through, the solution was washed with approx. 1 l of a 25% ammonia solution (1:10 in water).

The first peak at 200 ml elution volume contains PDE activity, and fluorescence.

Unreacted dye and unreacted PDE elute later.

* Testing for PDE activity:

400 μl eluate

600 μl trisbuffer pH 8.8/0.1M

200 μl Mg acetate 0.3M and

1000 μl bis-p-nitriphenyl phosphate, 1 mmolar are reacted for 105 mins. at 37° C., the reaction mixture becoming yellow in color.

EXAMPLE 15

Use of the marking reagent of Example 13 for gene probes

100 μg of the aminolink oligonucleotide with the sequence CTC GGA TCC CAT CTT CTC CCC TGA GTC TGT (synthesized in accordance with N. D. Sinha and R. M. Cook, Nucleic Acids Research 16, 2659 (1988) are dissolved in 300 μl carbonate buffer (pH 9) and an excess of polymeric fluorescent dye according to Example 13 in 200 μl carbonate buffer is added to the resulting solution. The reaction takes place over 60 h at room temperature. The reaction product is worked up by gel filtration using Biorad-Bio-Gel P 4 or by reversed phase HPLC using an RP 18 column with triethyl ammonium acetate/acetonitrile as eluent.

EXAMPLE 16

100 μg of the aminolink oligonucleotide with the sequence AT CTA CTG GCT CTT TTT TTT TTT TTT TTT TTT TTT TTT TIT T are dissolved in 200 μl carbonate buffer (pH 9) and an excess of polymeric fluorescent dye according to Example 13 in 300 μl carbonate buffer is added to the resulting solution, followed by stirring for 60 h at room temperature. For working up, the entire reaction mixture is applied to a Poly-A-Sepharose 4B column (5 ml) (Pharmacia), The non-bound dye is washed down with the application buffer (A) (see below, 20 ml), after which the column is washed with the elution buffer (B) (see below, 30 ml) and, finally, the coupling product is washed down with elution buffer (C) (see below, 40 ml).

Application buffer (A): dissolve 1,513 g tris, 10.23 g NaCl, 0.56 g EDTA in 750 ml water and make up with formamide to 1 liter.

Elution buffer (B): dissolve 7.45 g KCl in 100 ml application buffer A.

Elution buffer (C): make up 3.7 g KCl and 50 ml formamide to 100 ml with application buffer A.

The aminolink oligonucleotide thus marked may be directly used in DNA probe tests to detect a complementary nucleotide sequence.

We claim:

1. Compounds corresponding to general formula (I)

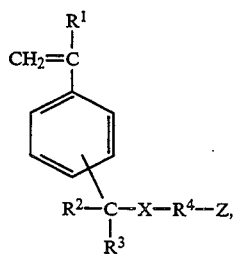
(I)

in which
X is NH—CO—Y or Y,
Y is NH, oxygen or sulfur,
Z is COOM or SO$_3$M,
M is hydrogen, sodium, ammonium or potassium,
R$^1$, R$^2$ and R$^3$ independently of one another represent hydrogen or methyl and
R$^4$ is C$_{1-12}$ alkylene, C$_3$ cycloalkylene, phenylene or naphthylene.

2. Compounds corresponding to formula (I) as claimed in claim 1, in which X represents NH—CO—NH or NH—CO—O; R$^1$, R$^2$ and R$^3$ represent methyl and R$^4$ represents C$_{2-11}$ alkylene or phenylene and the residue

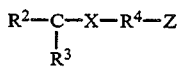

is in the meta position.

3. Compounds corresponding to formula (I) as claimed in claim 1, in which Z represents COOM and M stands for sodium, potassium or ammonium.

4. Compounds as claimed in claim 1, wherein X is NH—CO—Y, Y is NH, and Z is COOM or SO$_3$M.

5. Compounds as claimed in claim 1, wherein Z is COOM.

6. A compound as claimed in claim 1, consisting of a compound of the formula:

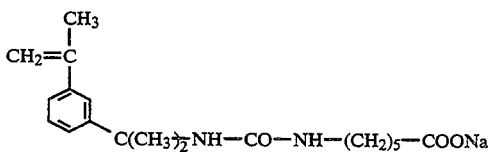

7. A compound as claimed in claim 1, consisting of a compound of the formula:

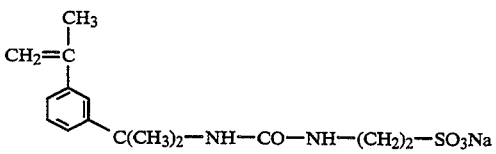

8. A compound as claimed in claim 1, consisting of a compound of the formula:

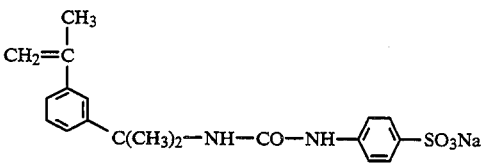

9. A compound as claimed in claim 1, consisting of a compound of the formula:

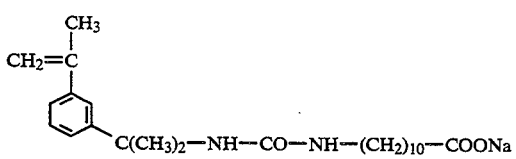

10. A compound as claimed in claim 1, consisting of a compound the formula:

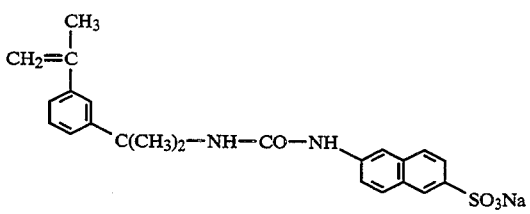

* * * * *